United States Patent [19]
Kutsch

[11] Patent Number: 6,149,895
[45] Date of Patent: Nov. 21, 2000

[54] DENTAL BLEACHING COMPOSITIONS, KITS & METHODS

[75] Inventor: V. Kim Kutsch, Jefferson, Oreg.

[73] Assignee: Kreativ, INC, San Diego, Calif.

[21] Appl. No.: 09/364,397

[22] Filed: Jul. 30, 1999

Related U.S. Application Data

[63] Continuation-in-part of application No. PCT/US98/02933, Feb. 17, 1998.

[51] Int. Cl.$^7$ ................. A61K 7/20; A61K 6/00
[52] U.S. Cl. ............................... 424/53; 433/215
[58] Field of Search ................. 427/53; 433/215

[56] References Cited

U.S. PATENT DOCUMENTS

| | | | |
|---|---|---|---|
| H534 | 10/1988 | Graham | 524/315 |
| 3,607,759 | 9/1971 | Barth | 252/100 |
| 3,966,669 | 6/1976 | Wolfe | 260/37 |
| 4,180,467 | 12/1979 | Barth | 252/99 |
| 4,302,439 | 11/1981 | Selwyn | 424/49 |
| 4,444,746 | 4/1984 | Harvey et al. | 424/49 |
| 4,661,070 | 4/1987 | Friedman | 433/203.1 |
| 4,788,052 | 11/1988 | Ng et al. | 424/53 |
| 5,032,178 | 7/1991 | Cornell | 106/35 |
| 5,055,048 | 10/1991 | Vassiliadis et al. | 433/215 |
| 5,240,415 | 8/1993 | Haynie | 433/216 |
| 5,256,402 | 10/1993 | Prencipe et al. | 424/53 |
| 5,281,141 | 1/1994 | Kowalyk | 433/215 |
| 5,430,074 | 7/1995 | Barnes et al. | 523/115 |
| 5,456,603 | 10/1995 | Kowalyk et al. | 433/215 |
| 5,645,428 | 7/1997 | Yarborough | 433/215 |
| 5,648,064 | 7/1997 | Gaffar et al. | 424/53 |
| 5,713,738 | 2/1998 | Yarborough | 433/25 |
| 5,785,527 | 7/1998 | Jensen et al. | 424/215 |
| 5,800,165 | 9/1998 | Kirsch et al. | 433/29 |
| 5,858,332 | 1/1999 | Jensen et al. | 424/53 |
| 6,036,493 | 3/2000 | Sharma | 433/216 |

OTHER PUBLICATIONS

Lee et al JL. Orthopedic Research 16(1) : 70–75 Lee et al Lasers In Surgery & Medicine 20(3):280–289, 1998, 1997.
Geibel Dtsch 2 ahn aer 212 50 (3):248–251 Staehle et al dtsch, Zahnarrltc 47(12): 832–835, 1992, 1995.
Palameda et al Scanning Micro Scopy 6(4) :1061–1071, 1992.
Smigel, Irwin "Laser Tooth Whitening" Dentistry Today, Aug. 1996.
QuasarBrite Advertising Flyer 19–1266–B.

*Primary Examiner*—Shep K. Rose
*Attorney, Agent, or Firm*—Lori M. Friedman

[57] ABSTRACT

A composition and method for bleaching teeth is disclosed wherein red dye is dissolved in a solvent and combined with an inert, inorganic carrier. The composition is mixed chairside by the dental practitioner, with a source of active oxygen to form a bleaching paste, which is applied to prepared teeth. Teeth coated with the paste are then exposed to light of a visible wavelength range of from 400–550 or an argon laser. When the active oxygen is spent, the bleaching paste on the teeth turns colorless. The red dye greatly accelerates the bleach time.

29 Claims, 1 Drawing Sheet

DENTAL BLEACHING COMPOSITIONS, KITS & METHODS

RELATED PATENT APPLICATION

This is a continuation-in-part patent application based on a PCT patent application Ser. No. PCT/US 98/02933 filed Feb. 17, 1998 and entitled "Dental Bleaching Compositions, a Kit, and Methods."

BACKGROUND OF THE INVENTION

The bleaching, or whitening, of teeth is a subject of much current interest in the dental community. Besides the pleasurable effects of white teeth, discoloration of non-vital teeth is often a consequence of endodontic treatment or in traumatized teeth which have experienced a loss of pulpal vitality. Vital teeth may become stained due to tetracycline prescribed for the patient for various medical reasons. Other causes of stained teeth may be drinking water with a high mineral content, caffeine drinks, and the use of tobacco products. Stains caused by these materials are not always removable by conventional prophylactic treatment. Conventional cleaning includes tooth brushing and/or the use of dental rinses.

There has been much recent interest in dentistry to whiten teeth. As discussed in *Reality, The Information Source for Esthetic Dentistry* 1996 edition, the available types of bleaching materials can be classified into three categories. These categories are power bleaching, assisted bleaching, and home bleaching.

Power bleaching materials contain high concentrations of hydrogen peroxide or other source of active oxygen. Most dental bleaches are applied as gels or pastes which are freshly prepared as needed in the dental operatory. Since hydrogen peroxide is a liquid, a powder is mixed with it for thickening. There may also be other ingredients present, such as catalysts or indicators. Light or heat is usually part of power bleaching.

In U.S. Pat. No. 5,240,415, Haynie discloses a dental bleaching system with separately compartmented hydrogen peroxide and fumed silica. Haynie is concerned with trays and storage compartments for the peroxide and carrier. There is no mention of any substances other than hydrogen peroxide and silica for bleaching. There is also no mention of heat or light in the bleaching process.

U.S. Pat. No. 5,645,428 to Yarborough utilizes peroxide mixed with a first catalyst applied to the tooth, after which the tooth is exposed to light from an argon laser. Next, a mixture of peroxide and a second catalyst are again applied to the tooth and irradiated with a carbon dioxide laser. This method employs a variety of other ingredients, including buffers, desensitizers, thickeners and the like. It also mentions the use of magnesium sulfate as a photocatalyst. There is no component of this bleaching composition with provides a distinct color change when the bleaching process is complete for that tooth.

A non-laser method for bleaching stained teeth by applying a concentrated solution of peroxide to stained teeth and focusing a beam of light at the teeth has been patented by Friedman in U.S. Pat. No. 4,661,070. The focused beam contains the combination of ultraviolet and infrared energy for activating the peroxide solution. There is no other chemical substance besides hydrogen peroxide in the Friedman patent.

Gaffar et al in U.S. Pat. No. 5,648,064 disclose a two component whitening dentifrice in which one component is a source of active oxygen and the second component activates the bleaching activity of the first component. The two components are maintained separately until the time of application to teeth. Besides the two components, there are various inactive components added to the dentifrice composition. Among these are humectants, vehicles, surfactants, thickeners, and colorants. The colorants may be pigments or dyes and may be distributed uniformly throughout the composition or be part of a striped dentifrice. In this case, it is clear that the color moieties are present for cosmetic purposes only.

QuasarBrite, manufactured by Interdent, Inc. is advertised as a combination of 35% hydrogen peroxide with thermal absorption crystals in a translucent, semi-viscous bleaching gel. It is advertised as complementary to the Argon laser. There is no mention of color change or any other indication of process completion.

Another composition for bleaching teeth comprises aqueous hydrogen peroxide and a multiplicity of components which are combined to treat the teeth in response to the application of optical energy as disclosed by Cornell in U.S. Pat. No. 5,032,178. This patent teaches the use of a gelling agent, an accelerator, a plasticizer/thickening agent, and a means for establishing a fixed time period for treating teeth in response to the application of optical energy. A redox indicator changes from green to colorless, indicating when bleaching is complete. It also indicates if the peroxide is still powerful enough to use for bleaching. The indicator is not said to accelerate, activate or in any way enhance the bleaching ability of the peroxide.

Recent technology in the dental bleaching art includes work by Jensen et al in U.S. Pat. Nos. 5,785,527 and 5,858,332. In both of these patents, the storage stability of the activated bleaching composition is emphasized. Various other ingredients are present in the bleaching compositions to help provide consistency and potency. There is no ingredient mentioned as a color change or other visual indicator of completion of bleaching.

Smigel, in an article in the August 1996 issue of *Dentistry Today* discusses laser tooth whitening in detail. In this article, he mentions that hydrogen peroxide is difficult to break down and unleash its full potential for tooth whitening.

Prior to the present invention, compositions and methods for whitening teeth required a significant amount of chair time for the patient. There was also a higher cost to the dental practice in terms of special equipment, time and supplies necessary for tooth whitening.

SUMMARY OF THE INVENTION

The present invention relates to power bleaching and it includes new dental bleaching compositions, kits containing these compositions, and methods of use. The bleaching composition of this invention is mixed with an aqueous solution providing active oxygen to form a paste that is applied to teeth. The paste is then exposed to light energy. A red dye in the bleaching composition greatly accelerates whitening of the teeth upon a brief exposure to the light. Furthermore, the dye changes color to indicate when the bleaching process is completed.

This invention has several features, no single one of which is solely responsible for its desirable attributes. Without limiting the scope of this invention as expressed by the claims that follow, its more prominent features will be discussed here briefly. After considering this discussion, and particularly after reading the section entitled "DETAILED DESCRIPTION OF THE PREFERRED EMBODIMENTS," one will understand how this invention provides safe, convenient, easy, comfortable, and rapid bleaching of teeth.

General

The bleaching composition comprises inert, non-toxic, inorganic carrier particles having absorbed thereon an effective amount of a red dye responsive to light that accelerates teeth whitening to decrease the time to bleach a tooth when the composition is exposed to light in the presence of active oxygen. For example, the carrier particles may be alumina, magnesium sulfate, or silica, amorphous fumed silica having a structure of a three dimensional branched chain aggregate with a particle length of 0.2 to 0.3 micron. Applicant has surprisingly discovered that a small amount of the red dyes added to carrier particles greatly accelerated the bleaching activity of the source of active oxygen. In this invention, the term 'active oxygen' will mean free radical oxygen. Not only does the active oxygen have enhanced activity for bleaching when used with the carrier particles, a red bleaching paste applied to the teeth becomes nearly colorless when the bleaching process is completed. This indicative color change is easily observed by the dental practitioner and allows more efficient use of both patient and dental staff time.

The red dye that accelerates the bleaching process which are the subject of this invention comprise a mixture of at least two red dyes dissolved in a suitable solvent, forming a solution that is mixed with carrier particles in a manufacturing facility. The carrier particles comprise an inert inorganic material which, when coated with dissolved red dye, become the dental bleaching composition of this invention. Carrier particles onto which the red dyes may be adsorbed may be alumina (aluminum oxide), florisil (magnesium sulfate), or silica (silicon dioxide). A preferred carrier material is silica. The preferred silica used in this invention typically has a structure of a three dimensional branched chain aggregate with a particle length of approximately 0.2 to 0.3 microns. An especially preferred silica is amorphous fumed silica.

The red dye typically comprises a mixture of red dyes, and the preferred dyes of the mixture are selected from the group consisting of Acid Red 92, Acid Red 388, and Quinaldine Red. In one embodiment the red dye is a mixture of Acid Red 388 and Acid Red 92 wherein the Acid Red 388 is the major constituent by weight and the Acid Red 92 is the minor constituent by weight. In another embodiment the red dye is a mixture of Quinaldine Red and Acid Red 92 wherein the Quinaldine Red is the major constituent by weight and the Acid Red 92 is the minor constituent by weight. The dye is dissolved in a solvent to provide a solution that is blended with the carrier particles to form a dry admixture of red dye on the carrier particles. the solvent is selected from the group consisting of isopropyl alcohol, ethyl alcohol, glycerol, and propylene glycol. The dye is present in the solution in an amount from 0.5 to 2 weight percent to the total weight of the solution. The admixture comprises from 10 to 20 weight percent of the dye solution.

A bleaching paste for teeth whitening is prepared comprising a source of active oxygen and the bleaching composition. The source of active oxygen may be hydrogen peroxide, carbamate peroxide, sodium perborate, calcium bicarbonate peroxide, or sodium bicarbonate peroxide. The preferred source of active oxygen is concentrated hydrogen peroxide solution comprising from 25 to 50 weight percent hydrogen peroxide and the balance water.

A kit is used to conveniently organize for the dental practitioner the bleaching materials and application tools. This kit includes two sealed containers. A first sealed container holds a predetermined quantity of the bleaching composition and a second sealed container holds a predetermined quantity of a liquid providing the source of active oxygen. The first sealed container is adapted to serve as a mixing vessel in which the contents of the first and second containers are mixed to form the bleaching paste to be applied to a patient's for teeth for whitening. Preferably, a package holds the first and second containers, and within the same package there are a tool for mixing carrier particles with the liquid to form the bleaching paste, a tool to apply a bleaching paste to teeth, a gingival protectant, and an applicator for the protectant. Preferably, the first container has a predetermined volumetric capacity sufficient to hold from 0.25 to 1.00 ounces of the bleaching composition. This first container is filled to at least 50 percent of said predetermined volumetric capacity. The second container has a predetermined volumetric capacity sufficient to hold from 1 to 3 cubic centimeters of the liquid. The containers are made of an opaque material that inhibits the transmission of light therethrough. One version of the kit is sized to hold only enough material to treat no more than two teeth. In this version there is only one lidded cup of particulate composition, one ampoule of liquid, one brush, one mixing stick, one tube of gingival protectant.

In accordance with the method of this invention for bleaching teeth, the bleaching paste is applied to a tooth and then the tooth with the paste thereon is exposed to light in the presence of the active oxygen. Light from different sources may be used and typically this light is not applied for more than two minutes per tooth. Light from an argon laser with an absorption band of from 457 to nanometers or visible light at wavelength from 400 to 550 nanometers may be used. In the case of the visible light the tooth is irradiated up to one minute per tooth. Preferably, these exposures are repeated for up to five times per tooth. The bleaching paste has a red color that becomes nearly colorless upon exposure to light for a predetermined period of time. The exposure of the tooth to the light is terminated when the bleaching paste becomes nearly colorless to indicate that the bleaching process is complete. The bleaching paste is freshly prepared at the time of applying the paste to the tooth by mixing the source of active oxygen and the bleaching composition.

The method of manufacturing the bleaching composition includes the steps of
 a) dissolving a red dye in a solvent forming a solution;
 b) delivering the red dye to carrier particles as a mist, preferably using a sprayer;
 c) mixing said solution with carrier particles;
 d) tumbling the mixture of solution and carrier particles in a tumble-type mixer until said solution is adsorbed onto said carrier particles.

Typically, from 8 to 16 ounces of the solution are added to 1.5 to 5 pounds of carrier particles. The solution and particles are typically tumbled together for a time period from 2 to 5 hours when the tumbling is ceased a dry admixture is formed.

DESCRIPTION OF THE DRAWING

The preferred embodiment of the kit of this invention, illustrating all its features, will now be discussed in detail. This embodiment depicts the novel and non-obvious kit of this invention as shown in the accompanying drawing, which is for illustrative purposes only. This drawing includes the following figures, with like numerals indicating like parts.

DETAILED DESCRIPTION OF THE PREFERRED EMBODIMENTS

Kits

Figure 1:
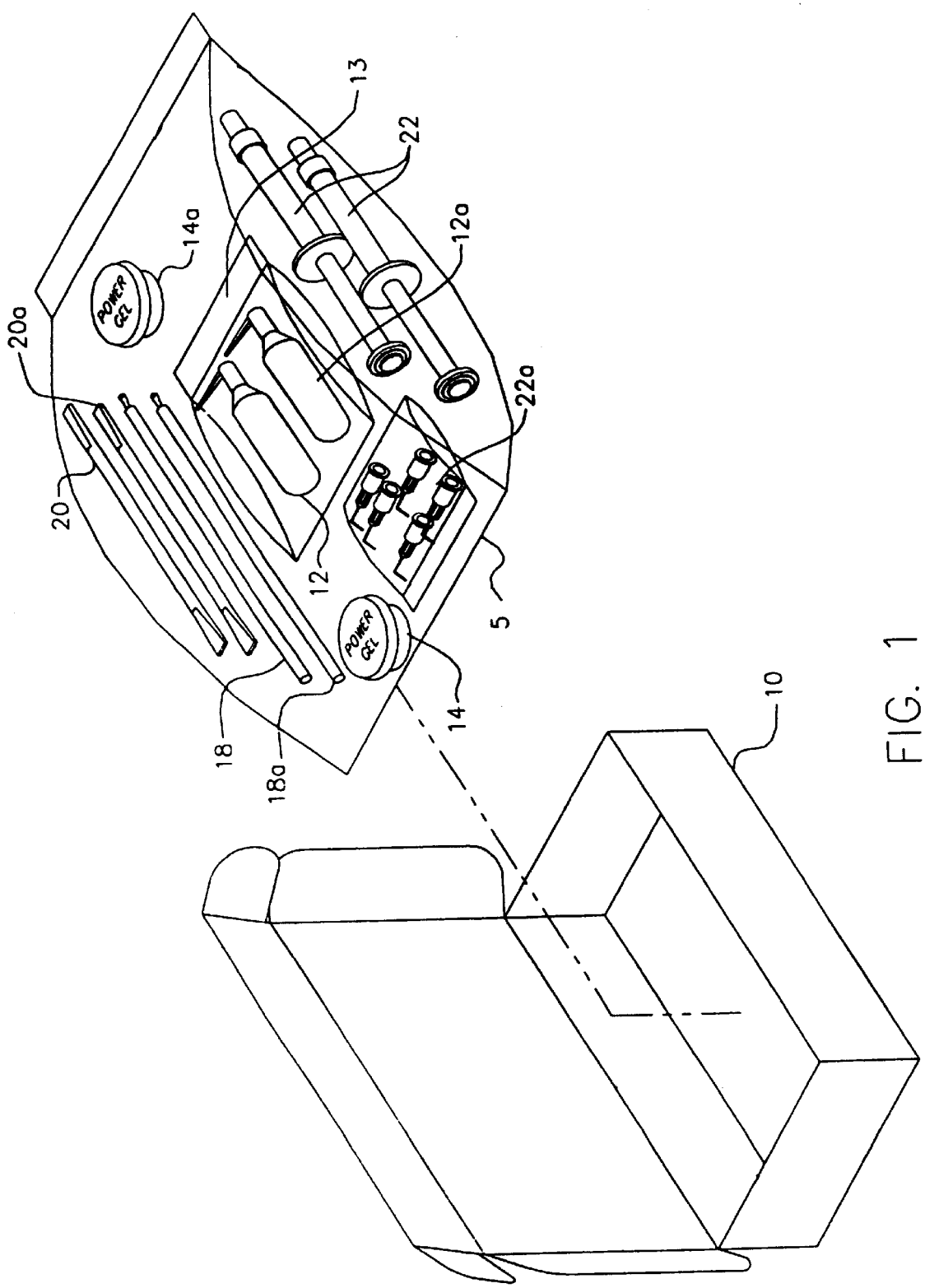
FIG. 1 is a perspective view of the kit of this invention.

The invention is best understood by reference to FIG. 1 that depicts a large kit 10 of this invention. The dental practitioner uses the kit 10 when he or she is performing the bleaching operation clinically. This invention also includes a small kit including all the components the dental practitioner needs to practice the bleaching method of this invention but with smaller capacity containers.

This kit 10 contains the materials and tools needed to whiten a pair of arches of teeth, one arch at a time. As shown in FIG. 1, kit 10 includes a package 5 such as a plastic bag packaged in a box 10 holding two lidded cups 14, two ampoules of active oxygen solution 12 in a baggy 13, two applicator brushes 18, and two stirrers such as mixing sticks 20. The kit also includes a 1 ml. syringe of gingival protectant 22 and at least two applicator syringe tips 22a. The materials of the kit are packaged in a plastic bag and the bag is packet in a cardboard box.

The kit 10 holds enough material to provide effective bleaching of at least two arches of dentition. As defined herein, an arch of teeth refers to either the top or bottom teeth in a patient's mouth. Usually the bleaching is desired on the teeth that are most visible. Besides the six top and six bottom teeth, whitening is sometimes desired on the neighboring teeth as well.

Each lidded cup 14 holds the bleaching composition of this invention. The lidded cups 14 also function as mixing vessels when the practitioner mixes the bleaching paste by emptying an ampoule 12 (about 2 cubic centimeters) of the liquid providing the active oxygen into the lidded powder cup 14. A mixing stick 20 may be used to mix the bleaching composition with the peroxide to form the bleaching paste. When the bleaching paste is then mixed, a brush 18 is used to apply the bleaching paste to the teeth of the arch being bleached.

The kit 10 also includes a syringe of Power Block™ gingival protectant, which is a dental dam material that shields the gums and other oral soft tissue from the bleaching composition. There are at least two syringe tips 22a included that are used to apply the dam material to the gingiva. There is enough protectant included in the kit 10 for at least two bleaching sessions. PowerBlock™ gingival protectant is a white, light-reflective, paint-on dental dam. It is cured by irradiation with blue visible light of wavelength ranging from 400–500 nanometers (nm) for a time period ranging from about 10–20 seconds at a power setting of a curing instrument of about 1.0 watts. Under these conditions, it forms a semi-plastic barrier that protects gingival tissue during in-office bleaching procedures.

This invention also is concerned with a smaller or 'touch-up' kit. This touch-up kit contains the same tools and materials disclosed above. The difference is that the touch-up kit contains a smaller package with less bleaching materials and fewer tools. The purpose of the touch-up kit is to treat one or two teeth when extra whitening is needed. More specifically, the touch-up bleaching kit contains only one lidded cup 14 of bleaching composition, one ampoule 12 of active oxygen solution, one brush 18, one mixing stick 20, one tube of gingival protectant 22 and two applicator syringe tips 22a. The bleaching composition fills at least 50% of the volumetric capacity of this cup 14.

When ready to bleach teeth, the dental practitioner mixes the contents of a lidded cup 14 with the liquid from the ampoule 12 to form the bleaching paste of this invention. The bleaching paste is easily and freshly prepared at chairside. In this invention "chairside" will mean while the patient is in the dental chair receiving treatment. Its ease of use is enhanced by having only two components. If concentrated hydrogen peroxide is used as the source of active oxygen, the solution will comprise from 25 to 50 weight percent of hydrogen peroxide.

Dyes

The red dye used in the composition of this invention is preferably a mixture of two red dyes. The mixture may be (a) two or more acid red dyes that are mixed with each other or (b) an acid red mixed with another type of red dye. Specifically, one type of red dye that may be used with the acid reds is a quinaldine red dye. The red dye mixture is mixed with a solvent, forming a solution that is mixed with carrier particles in a manufacturing facility. These particles of inert inorganic material coated with dissolved red dye become the dental bleaching composition of this invention. Acid red dyes are traditionally used in acid solution to dye fibers. The fibers may be wool, nylon or other fibers that are dyed in large-scale commercial fiber production. The color that these dyes impart to fiber is permanent.

A first preferred combination of acid red dyes include Acid Red 388 and Acid Red 92. Acid Red 388 that was used in this invention was made by DuPont and its structure is proprietary. It is a dark red powder soluble in alcohols and glycols. For the instant formulation, it was dissolved in propylene glycol and then combined with the second acid red dye, Acid Red 92. As described in *The Sigma-Aldrich Handbook of Stains, Dyes, and Indicators*, Acid Red 92 is a red, anionic, xanthene dye that is soluble in water and some glycols. Acid Red 92 is also known as Phloxine B, and is used industrially to dye wool from a weak acid bath, nylon from a formic acid bath, and silk from a neutral or acetic acid bath, to print wool and silk directly and to color stamping inks, lacquers, and paper. Acid Red 92 also displays indicator properties with a visual-transition interval from pH 1.1 (colorless) to pH 3.3 (purple). It has also been used as a fluorescent indicator from pH 3.4 (colorless) to pH 5.0 (yellow).

Preferably, the mixture of Acid Red 388 and Acid Red 92 in relative weight percentages of about 80% Acid Red 388 to about 20 weight percent Acid Red 92. A more preferred relative weight ratio is 85% Acid Red 388 to Acid Red 92. An even more preferred relative weight ratio is 90% percent Acid Red 388 to 10 percent Acid Red 92.

Another preferred red dye mixture of this invention that accelerates dental bleaching is likewise comprised of at least two components. The first component, which is the major component of the mixture, is quinaldine red. Quinaldine Red is a cationic, quinoline styryl dye that is very slightly soluble in water and ethanol. It is known and used as an acid-base indicator with a visual transition interval from pH 1.4 (colorless) to pH 3.2 (red). In the presence of chlorides, the visual transition interval shifts to pH 1.2 to pH 3.0. The other preferred red dye of the second bleach accelerating composition is an Acid Red dye. The particularly preferred Acid Red of the second composition of this invention is Acid Red 92, also known as phloxine B and described above. In the second preferred embodiment, the weight percentages of the Quinaldine Red is about 75% by weight. Acid Red 92 is present in about 25% by weight. Preferably, Quinaldine Red is about 85% by weight. Acid Red 92 is present in about 15%. Even more preferably, Quinaldine Red is about 88% by weight. Acid Red 92 is present in about 12%.

After the dye is dissolved in a suitable solvent, the amount of dye present may be as low as from about 0.5 to about 2% by weight of the solution. Preferably, is about one percent by weight of the total solution. Examples of these preferred solvents are isopropyl alcohol, ethyl alcohol, glycerol, or alkyl glycols. An especially preferred solvent in propylene glycol.

Certain of the above components are available commercially from the Aldrich Chemical Company, Milwaukee, Wis. For example, Acid Red 92, present in both preferred embodiments of the invention, has Aldrich Catalog Number 19,827-7. Acid Red 92 is also called Phloxine B, Cyanosin, and a variety of other common names. It is characterized as a red, anionic, xanthene dye. It is made by condensing two moles of resorcinol with one mole of tetrachlorophthalic anhydride to form 4,5,6,7-tetrachlorofluorescein. The tetrachlorofluorescein is then tetrabrominated in the 2',4',6' 7'-positions and that product is converted to the disodium salt.

Quinaldine Red has Aldrich Catalog Number 20,131-6. It is characterized as a light sensitive material. Quinaldine Red is a cationic, quinoline styryl dye that is very slightly soluble in water and ethanol. It is 2-4-dimethylaminostyrlquinoline ethiodide. This compound is made by condensing quinaldine ethyl iodide with 4-dimethylaminobenzaldehyde in ethanol in the presence of piperidine. It is known and used as an acid-base indicator with a visual transition interval from pH 1.4 (colorless) to pH 3.2 (red). In the presence of chlorides, the visual transition interval shifts to pH 1.2 to pH 3.0.

Both of these materials have optimal light absorption (lambda max) in the 500–600 range. As will be seen in the Examples that follow, these materials combine light sensitivity and reaction with active oxygen to accelerate the dental bleaching process of this invention.

Method Of Manufacture

The bleaching composition is made in a manufacturing facility by first preparing the dye solution and then mixing this solution with the carrier particles. The amount of dyes used is first weighed and then dissolved in propylene glycol. The solution is then blended in a tumbler with the carrier particles to form an admixture. The solution comprises about 15 weight of the admixture. The admixture is then tumbled for a sufficient time to thoroughly coat the particles with the solution. The admixture is the particulate composition of the present invention which is then packaged in lidded cups the factory for individual use by the dentist. The individual lidded cups each contain about a half-gram of the particulate composition.

Approximately from 8 to 16 ounces of the solution are added to 1.5 to 5 pounds of inorganic carrier particles. The solution and particles are then tumbled together for a time period of several hours, which time period typically exceeding 2 hours. More specifically, the tumbling of the dissolved dye and powder may range from 2 to 5 hours. When the tumbling is ceased a dry admixture is formed. This dry admixture is the particulate composition of this invention. From about 10 to about 20 weight percent of solution is included in the total weight of the mixture. In the manufacturing method of this invention used to form the dental bleaching compositions of this invention, an effective amount of the dye mixture is adsorbed on the carrier particles. The amount of dye is sufficient to rapidly bleach teeth upon exposure of the particulate composition to light energy in the presence of active oxygen.

Method Of Use

The bleaching paste of the present invention is a two component system: a concentrated source of active oxygen and a particulate composition having a red dye mixture adsorbed thereon. The concentrated active oxygen solution is a source of oxygen radicals. The source of oxygen radicals for dental bleaching is usually hydrogen peroxide. Concentrated hydrogen peroxide that is 30% or greater is a well-known and widely available dental bleaching material. Generally, in-office whiteners work more quickly than home bleaching products. This is due in part to higher concentrations and type of active ingredients, such as hydrogen peroxide.

Besides hydrogen peroxide, other sources of active oxygen are usable for dental bleaching with the components mentioned herein. For example, another widely used peroxide for dental bleaching is carbamide peroxide. Carbamide peroxide has a slower rate of reaction than hydrogen peroxide, especially at room and oral temperatures. Carbamide peroxide is ordinarily used for assisted bleaching in the dentists' office or as a boost in home bleaching. In these dental bleaching techniques, the results are less dramatic than those obtained with power bleaching. Additional source of active oxygen may be any peroxide selected from the group consisting of hydrogen peroxide, carbamate peroxide, peroxy acetic acid, sodium perborate, calcium bicarbonate peroxide, sodium bicarbonate peroxide, or any other alkali and alkaline earth metal oxides or oxygen radical generating agents. The solid sources of active oxygen will be mixed, chairside, with water and the red dye composition to form a bleaching paste. The preferred concentration of active oxygen is from about 30% to about 50%, although any concentration from about 3% to about 90% can be used. In power bleaching, hydrogen peroxide is most often used as a source of active oxygen. Active oxygen solubilizes stain molecules in tooth enamel and dentin to enable their removal. Once released from the tooth, the stains are dissolved into the saliva or an oral rinse.

In one preferred embodiment of the present invention, concentrated hydrogen peroxide is added to the particulate composition at the time of use in the dental operatory. This is in contrast to various prior art references discussed above, which maintain the storage stability of their bleaching agents. In this invention, the dental practitioner mixes the red bleaching paste chairside. Painting of the teeth with the red bleaching paste of this invention not only carries the peroxide to the tooth, its color change from red to colorless indicates when the bleaching process is complete by turning colorless after the tooth is exposed to light of certain wavelengths.

The bleaching composition, which is non-toxic, largely comprises an inert, powdered inorganic material such as amorphous fumed silica. Amorphous fumed silica is a colloidal form of silica that is a fine, white powder. Its chemical name is silicon dioxide, crystalline-free. It is often used as a thickener, thixotrope, and reinforcing agent in inks, resins, rubber, paint, cosmetics, and the like. In medical and dental applications, amorphous fumed silica has been used as a tabletting agent, as a dispersant in toothpastes, as a suspending agent, as an emulsion stabilizer in water/oil emulsions, as a glidant to aid the flow of pharmaceuticals, and as a powder free flow agent in such applications as foot powder. In this invention, preferred amorphous fumed silica is Aerosil 200 sold by the American Dental Hygenics company. An especially preferred amorphous fumed silica is Cab-O-Sil M-5 from the Cabot Corporation.

The use of amorphous fumed silica is not new to power bleaching. As has been previously stated, it has been used in power bleaching to forming a paste with a solution of hydrogen peroxide. The silica may be used as a non-reactive carrier that aids in the delivery of active oxygen to the tooth surface. Since amorphous fumed silica is inert to most chemicals, it is an ideal substrate for the indicating accelerating dyes used in the bleaching the composition of this invention. It is also well suited to its role as a thickener and carrier for concentrated active oxygen solution. When the dyes are dissolved in an organic solvent and added to amorphous fumed silica, the dye mixture is dried and adsorbed onto the amorphous fumed silica particles. This process is carried out in a manufacturing facility and is supplied to he dental customer as a pink powder.

In accordance with the method for bleaching teeth of this invention, the bleaching paste is applied to an arch of teeth and then exposing the teeth, with bleaching paste thereon, to light. High intensity visible light from a lamp or a laser may be used. Specifically, for each tooth irradiated with visible light with a wavelength of from 400–550 nanometers and a high power density of at least 800 milliwatts per square centimeter for a time period of about one minute per tooth, preferably repeated from one to four times per tooth. A preferred lamp apparatus is disclosed in U.S. patent application Ser. No. 09/004217, which is currently pending and is likewise assigned to Kreativ, Inc. This lamp apparatus is designed for both bleaching teeth and curing dental materials such as the gingival dam, as used herein. Both bleaching and curing modes of operation may be used in at least three different power levels designated as boost, ramp, and normal. The lamp apparatus contains a incandescent xenon-halogen bulb and a dichroic reflector which focuses filtered visible light on the end of a flexible light guide which is part a handpiece for directing the transmitted light by the light guide to the teeth.

If a laser is used, it must be an argon laser with an absorption band of from 457 to 515 nanometers for about two minutes per tooth. This procedure will be repeated from about one to four times per tooth. The bleaching paste has a red color when applied to the teeth. When the color of the paste becomes nearly colorless, the exposure of the tooth is terminated and the paste is applied to the next tooth of the arch. Specific steps of the bleaching process may be found below in the Examples.

Regarding active oxygen compounds, the ampoules 12 of the kit contain liquid providing the active oxygen. A preferred active oxygen source is concentrated hydrogen peroxide. In the kit 10 of this invention, hydrogen peroxide is provided in ampoules 12 having a volumetric capacity of about 2 cubic centimeters. A typical supplier is American Dental Hygenics, who supplies hydrogen peroxide of from 30–50% for dental use. The bleaching composition and the liquid hydrogen peroxide source are mixed freshly by the dental practitioner at chairside at the time of bleaching. To form the bleaching paste, the lidded cup 14 is opened and an ampoule 12 is opened. The contents of the ampoule 16 is emptied into the cup 14. The mix is then stirred with a mixing stick 20. This mix of liquid and bleaching composition is the bleaching paste.

After gingival protectant is applied, the teeth are painted with bleaching paste with brush 18. The paste applied to teeth is a red color. After the teeth are coated, they are exposed to visible light of a wavelength in the 400–550 nm range or light from an Argon laser. Argon lasers produce a narrow wavelength range of light from 457–515 nm. When the bleaching process is complete, the red color disappears. The disappearance of the red color in the bleaching paste is due to the transference of both heat and light from the red dye-containing activator powder to the peroxide to accelerate the bleaching process.

Light absorption in the visible and ultraviolet regions causes the excitation of electrons. Light in the wavelength range of 400–550 is the band of energy in which many red materials absorb light. Use of this frequency of light allows the red material to absorb energy from the light. This energy is subsequently transferred to the peroxide molecules present in the bleaching composition on the teeth. The transference of energy accelerates the bleaching power of the peroxide. The color changes from red to colorless as the bleaching is completed.

The wavelength at which a molecule absorbs light is a physical characteristic of that molecule. This absorption relates to the chemical structure and bonding of the electrons to the nucleus and is a distinct, measurable physical characteristic of a particular molecule. The excitation of the electrons by light of appropriate wavelength (referred to as lambda max) allows optimal, or maximum, absorption of energy by the electrons of the molecule. In the instant case, certain red dyes accelerate the bleaching activity of active oxygen materials in the presence of light of appropriate (400–550 nm) wavelengths. Bleaching activity is also accelerated when exposed to an Argon laser. The Argon laser has an absorption band of from 457 to 515 nanometers.

Some specific examples and comparative examples are presented to illustrate the composition and methods of the instant invention. These examples are meant to be illustrative purposes only and are not meant to limit the instant invention in any manner whatsoever.

EXAMPLES

The following Examples illustrate the method of bleaching teeth according to this invention. All the examples include using a the Kreativ Kuring Light set to "bleach" using visible light frequencies of 400–550 nm.

Patient Selection:

Normally, teeth may be classified into the following Vita shades or hues: A is brown discoloration, B is yellow discoloration, C is gray discoloration, and D is reddish discoloration. Each of these categories of discoloration is then classified on a numerical scale with lower numbers indicating less discoloration and higher numbers indicating more discoloration. It is therefore the object of bleaching procedures to grade the tooth color the lowest number possible. Patients with A (brown) or B (yellow) colorations normally have the best color improvement.

The practitioner should consider certain factors important when selecting patients for bleaching. Patients with yellow or brown stains of extrinsic origin will respond to the bleaching process with the fastest and best results. Tetracycline stains, fluorosis, and intrinsic mineral/metal stains are the most difficult to remove.

Patients with known thermal sensitivity, exposed dentin, large pulps, or leaky margins on restorations are not ideal candidates for bleaching using this process or any other bleaching process. Bleaching anesthetized teeth is contraindicated. Bleaching would be contraindicated for patients with porcelain or composite restoration in notable positions in the arch because the bleaching process will not lighten these restorations.

Patient Preparation:

The following preparative procedure was followed by the dental practitioner in all of the appended examples.

The dental practitioner is instructed to first coat the gums and other soft oral tissue with PowerBlock™ gingival protectant from syringe 22. This protectant shields the gums and other oral soft tissue from the bleaching composition. PowerBlock™ protectant is polymethyl methacrylate, made for Kreativ, Inc. by the Confidental Company. This cream-colored gel helps distinguish the gums from the teeth when the red activated bleaching composition is applied to the teeth. The protectant also absorbs heat that is generated by the bleaching process. It is also more comfortable for the patient than a rubber dam.

To apply PowerBlock™ protectant, the patient is fitted with cheek retractors. The practitioner removes the black liner cap from the syringe and replaces it with one of the syringe tips 22a. The teeth are rinsed and air-dried, after which a small amount of PowerBlock™ protectant is applied, beginning at one end of the arch. The amount applied to the gingiva will be about 6 millimeters (mm) wide by about one to one and one-half mm thick. The material is extended to the enamel by about one half mm. It is important to cover any exposed root surfaces and one extra tooth at the end of each arch to be bleached.

PowerBlock™ protectant is cured by irradiation with blue visible light of wavelength ranging from 400–500 nanometers for a time period ranging from about 5–15 seconds at a power setting of about 1.0 watts. The handpiece of the instrument is held about 3–5 mm from the applied material. Under these conditions, it forms a semi-plastic barrier that protects gingival tissue during in-office bleaching procedures.

Practitioners may want to test for patient sensitivity on a small section of the patient's gums before bleaching an arch. If there is any leftover protectant, it may be stored under refrigeration.

Bleaching Procedure:

The following bleaching procedure was followed by the dental practitioner in all of the appended examples.

1. The teeth are cleaned on labial and lingual surfaces with pumice. After this, they are rinsed well with water.
2. The tooth shade is measured and recorded using the standard technique of comparing the patient's tooth shade with standard Vita shade samples.
3. The patient is treated with cheek retractors, making sure of a comfortable fit.
4. Both the patient and the dental staff are fitted with amber safety goggles.
5. After recording the tooth shade, apply gingival, protectant, as described above.
6. To form the bleaching paste a lidded cup 14 is opened and an ampoule 12 of active oxygen compound is opened.
7. The contents of the ampoule 12 is emptied into the particulate composition cup 14 in the cup and stirred with a mixing stick 20. This mixture of active oxygen compound and particulate composition will be referred to as bleaching paste.
8. Using a brush applicator 18, paint the entire arch with bleaching paste. The thickness of the paste on the tooth surface should be about 2 mm.
9. The light apparatus that will be used must now be turned on. If there is a selector switch available to differentiate wavelengths of light, the selection must be to BLEACH mode. The wavelength of light selected must be in the 400–550 nm range. If a laser is used, it must be an Argon laser.
10. Begin bleaching at one end of the arch, holding the handpiece at a distance of 3 to 5 mm from the tooth. This is to ensure that the light from the lamp is a spot size that covers the entire tooth.
11. Expose each tooth in sequence to a 60 second (one minute) to the light. If the Kreativ Kuring Light is used, it will beep every minute in the BLEACH/NORMAL mode.
12. Steps 9 and 10 are followed for every tooth of the arch. As each tooth is exposed to light, the paste will change color from red to colorless indicating completion of the active oxygen bleaching of that tooth.
13. When all teeth of the arch have been exposed to the light for one minute each, wipe off the paste, rinse, and apply a fresh coat of paste to the arch.
14. Repeat steps 8–12, this time exposing first one tooth, then its contralateral counterpart, moving from the end of the arch to the midline. Using the above procedure will ensure that each tooth receives an equal cumulative exposure of three minutes.
15. Measure the post-op shade and compare with the pre-op measurement.
16. The patient should be cautioned against the use of any chromogenic foods or drinks (such as blueberries, coffee, or tea) for 48 hours.
17. A 48-hour recall visit should be scheduled. The teeth will usually become one Vita shade lighter during this time.

Example 1

Factory Preparation of a Composition of the Invention

Red dyes and Carrier Particles

Large-scale production of the composition of this invention takes place in a manufacturing facility. The end product is packaged and supplied to the dental practitioner as part of the kit 10, as described in FIG. 1, with the necessary ingredients and tools for bleach application.

Three and one-half pounds of CAB-O-SIL® M-5 untreated fumed silica was weighed and placed in a tumble-type mixer with a capacity of five and one-half cubic feet. The material is a light, fluffy powder. The mixer covered with a plastic lid and is then turned on.

A liquid containing 11 ounces of a red dye mixture dissolved in propylene glycol was delivered to the amorphous fumed silica using a sprayer that forms a mist. The dissolved red dye mixture may comprise a mixture of Acid Red 388 and Acid Red 92, or a mixture of Quinaldine Red and Acid Red 92 as has been described in the specification. Preferably, the dyes are about one percent by weight of the total solution. Misting ensures even and complete distribution of the red liquid solution and the amorphous fumed silica.

The mixer was run for about three hours. When stopped, the product was run through a sifter to remove and separate any large agglomeration of particles or clumps that may have formed during mixing. The mixer is run long enough to ensure thorough mixing and homogeneity throughout. After the mixing process is complete, the silica particles are a uniform pink color.

After sifting, the clump-free powder was transferred to 30-quart containers. Packaging of the activator powder was accomplished by placing an amount of about ½ tablespoon of powder into small, lidded plastic cups. The cup lids are then labeled. The filled cups are placed into date coded boxes for later assembly into the bleaching kit of the present invention.

The powder must be protected from light transmission until ready for use by the dental practitioner. The boxes that the kits are packaged in are dark colored. To accomplish an even higher degree of storage stability, the cups and lids should be made of opaque material. The dental practitioners should be alerted not to leave the pink powder exposed to light, but to re-cap the cup and store the lidded cup in the original box.

Tooth Bleaching via the Composition and Method of this Invention

Examples 2, 3, 4, and 5

Example 2

The patient in this case was a 33 year old female Caucasian. Her teeth were a reddish-gray hue, (D4 Vita shade) prior to the bleaching procedure of this invention. Her maxillary and mandibular anterior teeth ($1_{st}$ premolars, canines, and incisors) were bleached using paste made from Quinaldine Red: Acid Red 92 dye mixture(QR:AR). The light used to activate the bleaching paste was the Kreativ Kuring Light™ previously turned on and calibrated according to manufacturer directions.

Before the application of the bleaching paste, the patient's lips were retracted and her gingiva was coated with Kreativ PowerBlock™ gingival protectant. The barrier was applied in a strip 6 mm wide and 1–1.5 mm thick. The material was extended one half millimeter onto the enamel surface and extended to include one tooth at each end of the arch beyond those to be bleached. Care was taken to cover any exposed root surfaces with the barrier. The material was cured with the Kreativ Kuring Light™ for 10 seconds per tooth with the handpiece held 3–5 mm from the protective material. The curing process took approximately 80 seconds per arch.

The bleaching paste was prepared by mixing 1 ampoule of active oxygen solution 12 with the contents of one lidded cup 14 of bleaching composition provided in the kit 10 of this invention. Upon mixing, a thick reddish-pink paste was formed. The paste was then applied to the facial surfaces and over the edge of the incisal surfaces of the maxillary and mandibular anterior teeth using the applicator brush 18 supplied in the kit. The layer of paste was approximately 1 mm thick.

The Kreativ Kuring Light was used in the bleach mode set at the normal power level. The wavelength of light from this source is 400–550 nm. The tip of the light guide was brought within 4 mm of each tooth or until the spot size of the light encompassed the entire facial surface of the tooth. The light was applied to each tooth for 30 seconds. The paste changed from reddish-pink to clear during exposure to the light.

The paste was removed using high velocity suction and the teeth were rinsed thoroughly with water. The paste was then reapplied and the above process was repeated so that each tooth received 3 applications of paste.

In order to ensure that each tooth receives equal cumulative exposure to the light-activated paste, the light exposure for the first application is started at one end of the arch and extended across the arch. The second application of the light is started at the other end of the arch and extended in the opposite direction. The third application begins by exposing one tooth and then its contralateral counterpart, moving from each side of the arch to the midline.

At the completion of the procedure, the patient's premolars and canines had lightened dramatically from D4 to D2 on the Vita scale. The patient's incisors were lightened from D4 to a C1 on the Vita scale. The patient's incisors went from a shade of reddish-gray to a shade in a brighter hue in the gray family.

Example 3

The patient in this example was a 40 year old male Caucasian. His maxillary and mandibular anterior teeth (first premolars, canines, and incisors) were treated with bleaching paste including the red dyes (QR:AR). Prior to treatment, his teeth were a reddish-gray hue. His incisors were D2 on the Vita scale and his premolars and canines were a somewhat darker D3. The middle one-third of his maxillary canines had a darker band that appeared to be about D4.5 on the Vita scale. The etiology of this darker band is unknown.

The patient was prepared with gingival protectant according to the procedure specified in Example 2. The treatment with bleaching paste included three applications of the bleaching gel activated by the Kreativ Kuring Light™ in the normal bleach mode for 30 seconds per tooth for each application as was described in Example 2.

At the completion of the three applications, the patient's maxillary and mandibular canines remained a darker shade compared to the other teeth. A fourth application of bleaching paste was applied to the maxillary and mandibular canines and the Kreativ Kuring Light was applied for one minute per tooth. A fifth application of the bleaching gel was applied to the middle one-third of the maxillary canines only and the Kreativ Kuring Light in the normal bleach mode was applied for one additional minute per canine tooth.

After this series of treatments, all of the patient's maxillary and mandibular $1^{st}$ premolars, canines and incisors were D1 on the Vita scale. The patient experienced no thermal sensitivity or discomfort of any kind. The additional applications of bleaching paste to the maxillary and mandibular canines caused no discomfort and effectively lightened the patient's teeth and made them a uniform shade.

Example 4

The patient in this case was a 68 year old female Caucasian. The patient's maxillary and mandibular $1^{st}$ premolars, canines, and incisors were treated with bleaching paste made with red dye mixture (QR:AR). Prior to treatment, her teeth were A3 on the Vita shade scale. Her teeth showed a yellowish extrinsic discoloration on the interproximal and gingival areas of the incisors and canines, common to people her age. Her maxillary central incisors had darkly stained vertical cracks extending from the gingival margins to the incisal edges. The patient was considering porcelain veneers on the maxillary central incisors to improve her appearance.

The patient was prepared according to the procedure specified in Examples 2 and 3. Gingival recession around the maxillary and mandibular canines had exposed 3 mm of root surface on the facial surfaces of these teeth. During preparation, PowerBlock™ gingival protectant was extended to cover these areas. The treatment with QR:AR bleaching paste included three applications of the paste activated by the Kreativ Kuring Light™ in the normal bleach mode for 30 seconds per tooth for each application.

After the completion of three applications, the patient's maxillary canines remained slightly darker than the other teeth. A fourth application of the bleaching gel was applied to those teeth and the Kreativ Kuring Light in the normal bleach mode was applied for 30 seconds.

After completion of treatment with QR:AR bleaching paste, the patient's teeth had lightened to A1 on the Vita shade scale. The procedure of this invention removed the extrinsic yellow stains very effectively and lightened the overall yellowish intrinsic stains dramatically. The dark stains in the cracks on the maxillary central incisors were nearly eliminated. This bleaching technique dramatically lightened the patient's teeth and restored them to a more youthful appearance.

Example 5

The patient in this Example was an 8 year old boy. This patient had severe fluoride discoloration on the incisal third of his maxillary central incisors. Severe fluorosis had caused the patient's teeth to appear dark brown, approximately an A8 on the Vita scale.

The patient's gingiva was protected according to the procedure specified above. Treatment included four applications of the activator/bleach composition of this invention. The paste was made using paste made from a mixture of Acid Reds 388 and 92 in weight proportions of about 9:1 Acid Red 388: Acid Red 92. (AR:388:AR 92). The paste was applied, and the teeth were irradiated by light in the 400–550 nm wavelength. For this patient, light was from the Kreativ Kuring Light™ set at the boost power level for 1 minute per tooth.

After a series of treatments, the child's teeth measured A2.5 on the Vita shade scale. The boy experienced no thermal sensitivity or discomfort of any kind. This was an example of the dramatic color change possible using the composition and methods of this invention. Due to the severe discoloration, four repetitions of the paste application/light irradiation were performed.

The boy's teeth were so badly discolored that prior to performance of the bleaching procedure, application of veneers were the recommended dental treatment plan. The appearance of his teeth after the bleaching treatment negated the need for any painful and expensive treatment to improve his appearance.

It is noted that in the preceding examples, the paste was applied at least three times. Each application was followed by irradiation of light. The process may be repeated anywhere from one to five times. The number of times that the process is repeated depends on several factors. These factors include the severity of tooth discoloration, the number of porcelain crowns that the patient has is the arch being bleached, and other factors that vary from patient to patient.

The amount of time for the bleaching process to be performed, about 30 seconds per tooth, is minor when compared to the entire office visit for bleaching, including application of gingival protectant, determining pre- and post-bleach Vita shades, and pre- and post bleaching photography.

Comparative Example A

Comparative Example A: Use of Hydrogen Peroxide and Amorphous Fumed Silica to Bleach Teeth The patient in this case was a Caucasian male of 55, the initial tooth color was rated as Vita shade 3.5A. The teeth were cleaned and prepared according to the procedure detailed above. Before mixing and applying the bleaching paste, gingival protectant was applied and cured with the Kreativ Kuring light. This light was used for about 10 seconds per tooth for a total of about 60 seconds, or one minute, to cure the dam on the mandibular (lower) arch of this patient.

The bleaching procedure was performed using plain, untreated amorphous fumed silica without the use of any red dye. The plain white powder was mixed with concentrated hydrogen peroxide (35%) in the identical fashion as detailed in the examples above with dye-activated powder.

The peroxide/silica paste mixture was applied to the teeth. Light in the range of 400–550 nm was irradiated on each tooth for a time period of one minute per tooth. This application/irradiation procedure was repeated three times per tooth.

This patient's final shade was measured on the Vita scale as 3.0A. The change from 3.5A to 3.0 was hardly discernible. This example markedly distinguishes the difference between the paste made with red dye/silica paste and the silica used with just hydrogen peroxide.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

What is claimed is:

1. A bleaching composition comprising carrier particles comprisina an inert, non-toxic, inorganic material, and adsorbed on the carrier particles an effective amount of a mixture of at least two red dyes responsive to light that accelerates teeth whitening to decrease the time to bleach a tooth when the composition is exposed to light in the presence of active oxygen.

2. The bleaching composition of claim 1 wherein the red dye mixture comprises Quinaldine Red and Acid Red 92.

3. The bleaching composition of claim 2 wherein the Quinaldine Red is the major constituent by weight and the Acid Red 92 is the minor constituent by weight.

4. The bleaching composition of claim 1 wherein the mixture of dyes is dissolved in a solvent to provide a solution which is blended with the carrier particles to form a dry admixture of red dye adsorbed onto the carrier particles.

5. The bleaching composition of claim 1 wherein the inorganic material is silica.

6. The bleaching composition of claim 4 in which from 10 to 20 weight percent of solution is included in the total weight of the admixture.

7. The bleaching composition of claim 4 wherein the solvent is propylene glycol.

8. The bleaching composition of claim 4 wherein the dyes are present in the solution in an amount from 0.5 to 2 weight percent to the total weight of the solution.

9. The bleaching composition of claim 4 wherein the carrier particles are amorphous fumed silica having a structure of a three dimensional branched chain aggregate with a particle length of 0.2 to 0.3 micron.

10. A bleaching paste for teeth whitening comprising
   a) a source of active oxygen, and
   b) a bleaching composition comprising carrier particles comprising an inert, non-toxic, inorganic material, and adsorbed on the carrier particles, an effective amount of a mixture of at least two red dyes responsive to light that accelerates teeth whitening to decrease the time to bleach a tooth when the bleaching paste is exposed to light in the presence of active oxygen,
   said bleaching paste being red in color when applied to the teeth and becoming nearly colorless when the bleaching process is completed.

11. The bleaching paste of claim 10 wherein the source of active oxygen is hydrogen peroxide.

12. The bleaching paste of claim 11 wherein the hydrogen peroxide is an aqueous, concentrated solution comprising from 25 to 50 weight percent hydrogen peroxide and the balance water.

13. The bleaching paste of claim 10 wherein the carrier particles are amorphous fumed silica having a structure of a three dimensional branched chain aggregate with a particle length of 0.2 to 0.3 micron.

14. A kit including
   a first sealed container holding a predetermined quantity of a bleaching composition comprising carrier particles, and on the carrier particles is adsorbed an effective amount of a mixture of at least two red dyes responsive to light that accelerates teeth whitening to decrease the time to bleach a tooth when the composition is exposed to light in the presence of active oxygen;
   said first container having a predetermined volumetric capacity sufficient to hold from 0.25 to 1.00 ounces of the bleaching composition, and being filled to at least 50 percent of said predetermined volumetric capacity,
   a second sealed container holding a predetermined quantity of a liquid providing a source of active oxygen,
   said first sealed container being adapted to serve as a mixing vessel in which the contents of the first and second containers are mixed to form a bleaching paste to be applied to a patient's for teeth for whitening.

15. The kit of claim 14 including a package holding said first and second containers, and within the same package a plurality of tools for mixing carrier particles with the liquid to form the bleaching paste, a tool to apply a bleaching paste to teeth, a gingival protectant, and an applicator for the protectant.

16. The kit of claim 14 wherein the containers are made of an opaque material that inhibits the transmission of light therethrough.

17. The kit of claim 14 wherein the containers are sized to hold only enough material to treat no more than two teeth.

18. A method for bleaching teeth comprising
   applying to a tooth a bleaching paste including (a) a source of active oxygen, and (b) a bleaching composition comprising carrier particles comprising an inert, non-toxic, inorganic material and adsorbed on the carrier particles an effective amount of a mixture of red dyes responsive to light that accelerates teeth whitening to decrease the time to bleach a tooth when the composition is exposed to light in the presence of active oxygen, and
   exposing the tooth to light.

19. The method of claim 18 wherein the red dye is a mixture of Quinaldine Red and Acid Red 92.

20. The method for bleaching teeth of claim 18 wherein the tooth is irradiated with laser light from an argon laser with an absorption band of from 457 to nanometers for up to two minutes per tooth.

21. The method for bleaching teeth of claim 20 wherein the exposing step is repeated up to five times per tooth.

22. The method for bleaching teeth of claim 18 wherein the tooth is irradiated with visible light at wavelength from 400 to 550 nanometers for up to one minute per tooth.

23. The method for bleaching teeth of claim 18 wherein the bleaching paste has a red color which becomes nearly colorless upon exposure to light for a predetermined period of time, and the exposure of the tooth to the light is terminated when the bleaching paste becomes nearly colorless to indicate that the bleaching process is complete.

24. The method for bleaching teeth of claim 23 wherein the predetermined time period is no more than two minutes.

25. The method for bleaching teeth of claim 18 where the bleaching paste is freshly prepared at the time of applying the paste to the tooth by mixing the source of active oxygen and the bleaching composition.

26. The bleaching composition of claim 1 wherein the mixture of at least two red dyes becomes nearly colorless when exposed to light in the presence of active oxygen.

27. The method of claim 18 wherein the mixture of red dyes comprises Quinaldine Red and Acid Red 92.

28. The bleaching paste of claim 10 wherein the mixture of red dyes comprises Quinaldine Red and Acid Red 92.

29. The kit of claim 14 wherein the mixture of red dyes comprises Quinaldine Red and Acid Red 92.

* * * * *